United States Patent [19]

Kueppers

[11] 4,053,748

[45] Oct. 11, 1977

[54] TECHNIQUES FOR DETERMINING THE PEAK ANGLE OF RESPONSE OF PIEZOELECTRIC CRYSTALS AND OTHER RADIATION-SENSITIVE RESONANT DEVICES

[76] Inventor: Horst William Kueppers, 126 Brewster Ave., Piscataway, N.J. 08854

[21] Appl. No.: 636,435

[22] Filed: Dec. 1, 1975

[51] Int. Cl.² .............................................. G01N 23/20
[52] U.S. Cl. .................................... 364/525; 250/273; 364/563; 364/527
[58] Field of Search ........................ 235/151.3, 151.31; 444/1; 250/272, 273, 279; 324/80, 81, 82

[56] References Cited

U.S. PATENT DOCUMENTS

| | | | |
|---|---|---|---|
| 3,448,265 | 6/1969 | Samuelson | 250/272 X |
| 3,736,426 | 5/1973 | Anderson et al. | 250/273 |
| 3,870,880 | 3/1975 | Merigoux et al. | 250/273 |
| 3,934,138 | 1/1976 | Bens | 250/272 X |

Primary Examiner—Edward J. Wise

[57] ABSTRACT

A technique for inspecting a quartz or other cut piezoelectric crystal to determine its angle of peak response to an incident beam of X-radiation is described. A reference surface of the crystal is stepped with respect to the beam through equal angular intervals, and the output of a scintillation counter responsive to the accumulated reflected radiation pulses from the crystal is sampled at the end of each step. Successive samples which exceed a threshold on the leading edge of the crystal response curve during the step scan are stored in a memory, together with the attained values of scanned angle at the end of each step. When a monotonic decrease of such stored samples over at least two successive steps is detected, the stored sample occurring two steps previous to such detection is retrieved from memory, and is multiplied by first and second fractions to yield upper and lower boundaries of a predetermined "valid data" range. When the succeeding samples have decreased in amplitude to the upper boundary of such range on the trailing edge of the crystal response, the memory is again scanned to retrieve a previously stored pair of samples that occurred on the leading edge of the response characteristic and that straddled the amplitude of the then-occurring sample on the trailing edge. For each such successive pair of retrieved samples, an angle corresponding to an amplitude equal to the amplitude of the then-occurring sample on the trailing edge is derived, and such derived angle is added to the attained angle corresponding to the then-occurring sample on the trailing edge to form a first sum. The first sums occurring over the total number of steps spanning the valid data range on the trailing edge are accumulated and are divided by twice the number of such steps to approximate the peak angle of response of the crystal.

14 Claims, 5 Drawing Figures

TECHNIQUES FOR DETERMINING THE PEAK ANGLE OF RESPONSE OF PIEZOELECTRIC CRYSTALS AND OTHER RADIATION-SENSITIVE RESONANT DEVICES

BACKGROUND OF THE INVENTION

The invention relates to the determination of the angle of peak amplitude response of a radiation-sensitive resonant device, and more particularly to facilities and techniques for determining the angle of peak reflection, from a prescribed internal atomic plane of a crystal, of an X-ray beam incident on the atomic plane through a reference surface of the crystal as the reference surface is scanned by such beam.

Highly accurate electronic frequency sources employ cut piezoelectric crystals, such as quartz crystals, to determine a unique, ultrastable reference frequency. Such cut crystals have a planar reference surface which, for each desired reference angle, is cut at a predetermined angle with respect to at least one atomic plane within such crystal. (The angle between the reference surface and the atomic plane defines what is commonly known in the art of AT-cut quartz crystals as the "Z—Z' angle"). Since differences in such angle will produce corresponding differences in the temperature-frequency characteristics of the crystal, it is important when mass-producing such crystals to determine rapidly and accurately the value of such angle in order to sort the successive crystals into batches corresponding to the different temperature characteristics.

Present automated arrangements for accomplishing this function employ an X-ray diffraction technique, whereby the test crystals are positioned on a crystal mount associated with a rotating spindle of a goniometer. The crystal is mounted for rotation about an axis parallel to the reference plane, and such surface is scanned by rotating the spindle through a prescribed angle with respect to a highly collimated, X-ray beam which is incident on the atomic plane of the crystal through the reference surface. The angle of scan includes the range encompassing the resonant-type response characteristic of the crystal.

The resulting radiation is reflected from the atomic plane via the reference surface, and the accumulated pulses picked up by the detector correspond to the amplitude response of the crystal at that point of the scan.

During the rotation of the spindle, a shaft encoder coupled thereto indicates the attained angle of scan as the detector accumulates the reflected pulses. The output of the detector is coupled to a peak sensing circuit. As the crystal is scanned over the peak region of the crystal response, the peak sensing circuit sends a triggering signal to the shaft encoder which outpulses a digital quantity indicative of the peak angle at which the detector response is optimum, and such angle is recorded automatically or manually. The outpulsed digital signal from the encoder also operates a suitable sorting device which discharges the tested crystal into an appropriate bin corresponding to the attained angle of the peak response for the purposes indicated above. Alternatively, when the measured peak angle falls outside a predetermined range, the crystal may be rejected.

Such existing types of automated crystal inspection apparatus have several disadvantages, which are related principally to the fact that the X-ray diffraction technique employed is statistical in nature. That is, as the reference surface of the crystal is angularly scanned over the resonant characteristic, the multiplier-type detection tube counts and integrates the number of essentially random pulses that are reflected toward such detector from the atomic plane of the crystal as an indication of reflected intensity. In general, the multiplier tube output does not reach a steady state before the crystal mount advances beyond the associated angle; and as a result, the range of statistical error in the integrated pulse count at each attained angle of scan can overlap the integrated pulse count at the preceding and succeeding angles of scan, thereby leading to a multi-valued rather than a monotonic measured characteristic.

The statistical errors indicated above have relatively little effect when measurements are taken on a crystal having a sharp reflected intensity characteristic, since even in the peak regions of such characteristic the mean differences in the accumulated number of reflected pulses detected between two points of attained angle during the scan are large enough to exceed the normal range of statistical error at any given point in the scan. Thus, when the peak portion of the curve is sharp, i.e., when the test crystal has already undergone a succession of expensive lapping and polishing operations after its initial cut from a mother crystal, the desired angle of peak response of the device can be determined with acceptable accuracy, since the successive measured points around the sharp peak differ sufficiently in amplitude from each other to fall outside the statistical error.

However, when such peak is relatively broad, as is the case when testing crystals in the early stages of processing where their rejection would entail relatively small expense, the existing peak-seeking techniques are inaccurate, since the output of the scintillation counter in the region about the peak will constantly be subjected to an error greater than the mean difference in amplitude of successive points around the peak. As a result, the angle read-out by the shaft encoder when triggered by the peak detector will be unpredictable as an indication of the desired peak angle.

SUMMARY OF THE INVENTION

Such disadvantages are overcome with the facilities of the present invention, which are adapted to rapidly and automatically approximate, within extremely close limits, the peak angle of response of a quartz or other piezoelectric crystal at an early stage of crystal processing where the peak region of the response curve is broad and therefore unsuitable for extremely accurate inspection by presently known peakdetection techniques. With such improved facilities, crystal processing is made more efficient and inexpensive, and exhibits an enhanced yield of properly sorted and acceptable crystals.

In an illustrative technique, the reference surface of the test crystal is scanned stepwise by an X-ray beam through equal angular intervals. At the conclusion of each step, the output of the pulse detector is sampled. As soon as a reflected amplitude value indicative of a pre-set threshhold level is detected on the leading edge of the response curve, the succeeding samples are applied to suitable addresses of a memory. Simultaneously, the output of a shaft encoder or other attained angle indicating device representing the attained angle at which each amplitude sample was taken is applied to a separate address in the memory.

When the amplitude of the successive stored samples has decreased monotonically over a prescribed number, (e.g., two) of successive steps, a command signal is applied to the memory to outpulse from the appropriate address a first one of the stored amplitude samples whose corresponding attained angle occurred at the end of the predetermined number of steps prior to the occurrence of the command signal. Such last-mentioned retrieved sample is assigned as the "peak" value of the response curve. Such outpulsed sample is respectively multiplied by fractions indicating the upper and lower boundaries of a preassigned "valid data range" of the crystal response characteristic, such range illustratively lying between 87½% and 50% of the amplitude of the retrieved sample. Such range, which excludes the area immediately around the peak, encompasses the region of maximum slope, positive or negative, of the response characteristic.

The sampling continues down the trailing edge of the response characteristic from the retrieved "peak" until the sample amplitude has reached the upper limit of the valid data range. At this point, a scan of the addresses in the memory is started, whereby each sample occurring within the valid data range on the trailing edge of the characteristic is compared with each of the previously stored amplitude samples occurring on the leading edge of the characteristic and corresponding to amplitudes within the valid data range.

For each such comparison, there is retrieved a successive pair of stored samples which have amplitudes immediately greater and less than the amplitude of the sample then occurring along the trailing edge. From the attained angles corresponding to the retrieved pair of samples, there is derived, by interpolation or other suitable technique, a first one of the attained angles on the leading edge of the characteristic which corresponds to an amplitude value substantially equal to the value of the amplitude sample taken during the then-occurring step on the trailing edge. Each such first angle is added to a second one of the attained angles corresponding to the present amplitude sample on the trailing edge to form a first sum.

The first sums are accumulated over the number of steps occurring during the valid data range on the trailing edge, and the accumulated value of such sums is divided by twice the number of such steps to approximate the angle of peak reflection intensity of the crystal response curve.

With such technique, it has been found possible to determine the peak angle of response of a coarsely processed crystal with the same or greater accuracy as that obtainable with prior-art measurements taken with the direct peak-seeking apparatus on much more finely processed crystals. Such improvements have been found to be essentially unaffected by the surface condition of the crystal, the geometry of the equipment used, and the precise configuration of the peak of the crystal response.

BRIEF DESCRIPTION OF THE DRAWING

The invention is further set forth in the following detailed description taken in conjunction with the appended drawing, in which.

DETAILED DESCRIPTION

Figure 1:
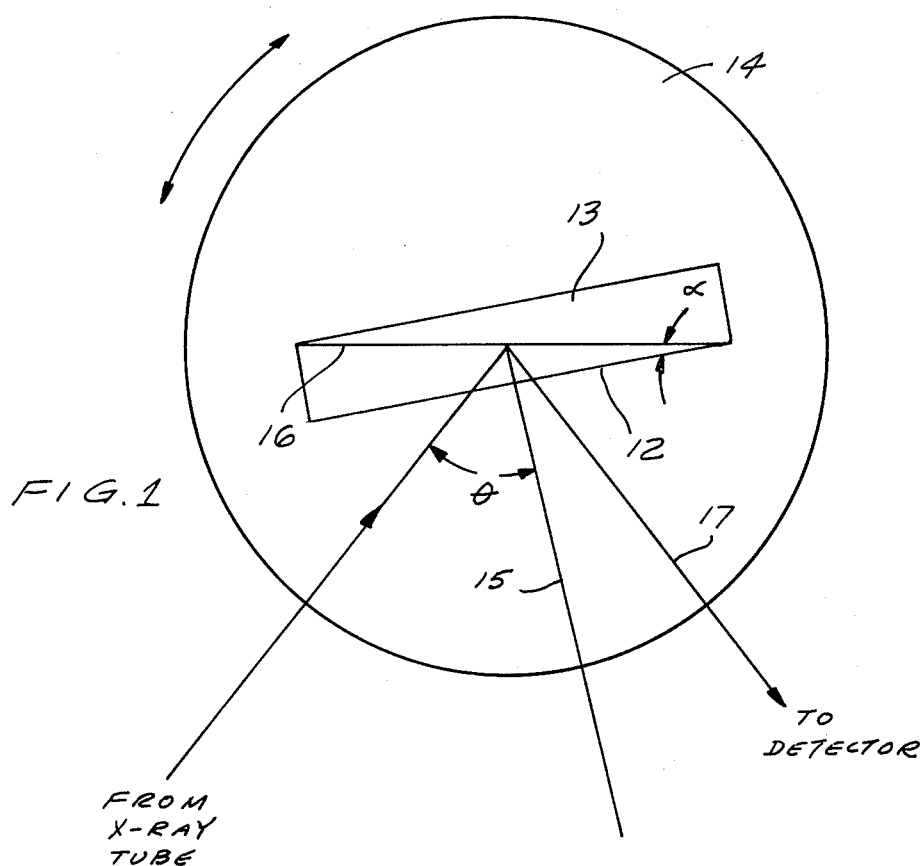
FIG. 1 is a highly stylized view of a cut quartz crystal to be inspected with the facilities of the present invention, illustrating the angles of incidence and reflection of a collimated pulsed X-ray beam with respect to a typical atomic plane and reference surface of the crystal.

Referring now to the drawing, FIG. 1 illustrates a collimated X-ray beam 11 which is directed toward a reference surface 12 of a cut quartz crystal 13 whose angle of peak reflection intensity relative to the beam 11 is to be determined. The crystal 13 is suitably mounted on a rotatable crystal mount 14 of a conventional X-ray goniometer, which may be of the type disclosed, e.g., in U.S. Pat. No. 2,585,916 or U.S. Pat. No. 3,448,265.

The beam 11 passes through the reference surface 12 at an angle $\theta$ relative to a normal 15 to the surface 12, and impinges upon an atomic plane 16 within the crystal. The atomic plane 16 forms, with the reference surface 12, an angle $\alpha$ indicative of the Z—Z' angle of the crystal. Such angle is indicative of the temperature-frequency characteristic of the crystal 13, and thereby of the bin (not shown) to which such crystal is to be discharged from the goniometer after test for ultimate incorporation, e.g., in electronic frequency generators having a stabilized reference operating frequency corresponding to such temperature characteristic. Further details of the nature and significance of the Z—Z' angle is discussed in U.S. Pat. No. 3,736,426, and will not be discussed further here.

The determination of the Z—Z' angle is facilitated, in the general case, by a determination of the angle $\theta$ at which the intensity of a reflected X-ray beam 17 exiting from the crystal via the reference surface 12 is maximum. Since the Bragg angle of reflection from the atomic plane 16 is fixed, the determination of the angle $\theta$ of peak reflection with respect to the normal 15 to the surface 12 permits a simple calculation of the desired Z—Z' angle and thereby of the bin to which the tested crystal is to be discharged.

The crystal mount 14 is mounted for rotation about an axis perpendicular to the plane of the drawing, and is suitably moved through successive angles $\theta$ through a range which accommodates the normal response characteristic (designated 21 in FIG. 2) of the crystal 13, so that the angle of the peak crystal response during such movement can be determined in the manner described below.

Presently known methods of determining the angle of peak response associates a peak determination circuit with an X-ray pulse detector, illustratively a scintillation counter or other radiation detector, which yields an indication of the intensity of reflection by integrating the number of essentially random pulses reflected from the atomic plane 16 and directed toward such pulse detector. During continuous rotation of the crystal mount 14 in such arrangements, the time for accumulation of reflected pulses at any given attained angle of the crystal mount is relatively short, so that the above-described statistical error in the accumulated count at one instant may overlap the accumulated counts determined during the preceding and succeeding instances. Therefore, in the peak portion of the curve 21 (FIG. 2), i.e., the region within 10% or so of the "peak", the rate of change of the intensity values determined by the scintillation counter is quite small, and the successive measurements over the peak are swamped in statistical error.

Also, the collimated beam 11, when an X-ray tube having a conventional copper target is used, actually contains two characteristic output frequencies that are very close together. Consequently, the individual Bragg angles of reflection corresponding to the two closely spaced nominal frequencies of the X-ray tube will cause in effect two separate reflected beams 17 to emerge from the crystal 13, each of the separate beams exhibiting a peak at a slightly different angle. Accordingly, the superimposed responses of the scintillation counter to such slightly separated beams will be even more flattened and distorted, further aggravating the statistical problem mentioned above.

As a result, the existing peak-seeking techniques can approach the accuracy necessary for highly efficient crystal sorting only when the peak regions themselves are extremely sharp, a phenomenon that will normally occur only after the crystal has already been subjected to a plurality of expensive processing steps.

In accordance with the invention, the angle of peak response of a tested crystal can be obtained at a very early stage of crystal processing where the peak region of the crystal response is relatively flat and thereby normally subject to errors of the type that render conventional inspection techniques comparatively inefficient.

Figure 3:
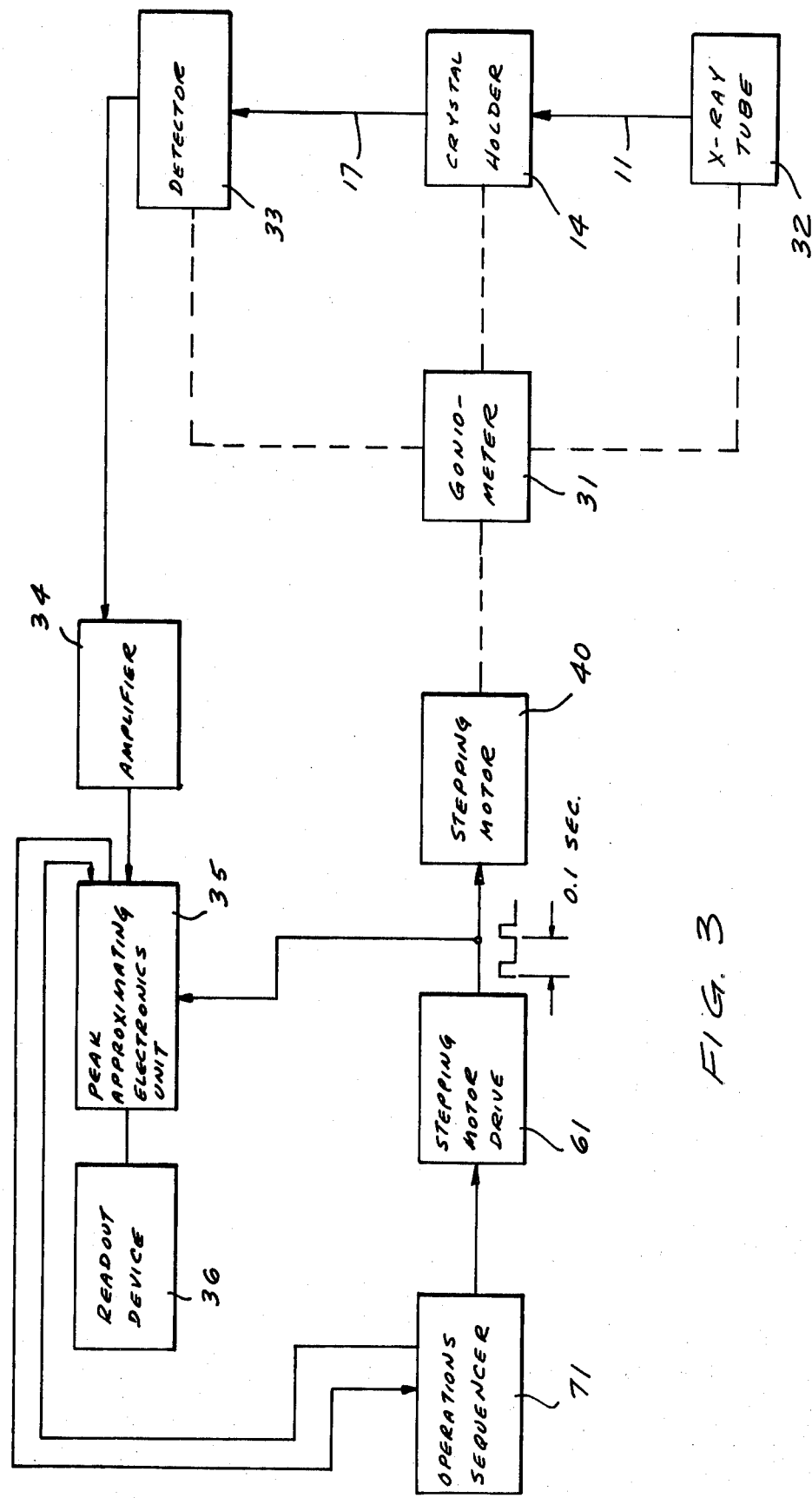
FIG. 3 is a block diagram of an illustrative arrangement in accordance with the invention for approximating the angle of peak intensity of the response curve of FIG. 2.

An illustrative arrangement of the crystal inspection technique of the present invention is depicted in FIG. 3. The crystal holder is shown associated with a conventional goniometer 31, to which is coupled a conventional copper-target X-ray tube 32. The tube 32 emits the collimated X-ray beam 11 toward the crystal (not shown) mounted on the holder 14, and the reflected beam 17 from the crystal is applied to an X-ray detector 33, illustratively a scintillation counter or other radiation detector.

Figure 2:
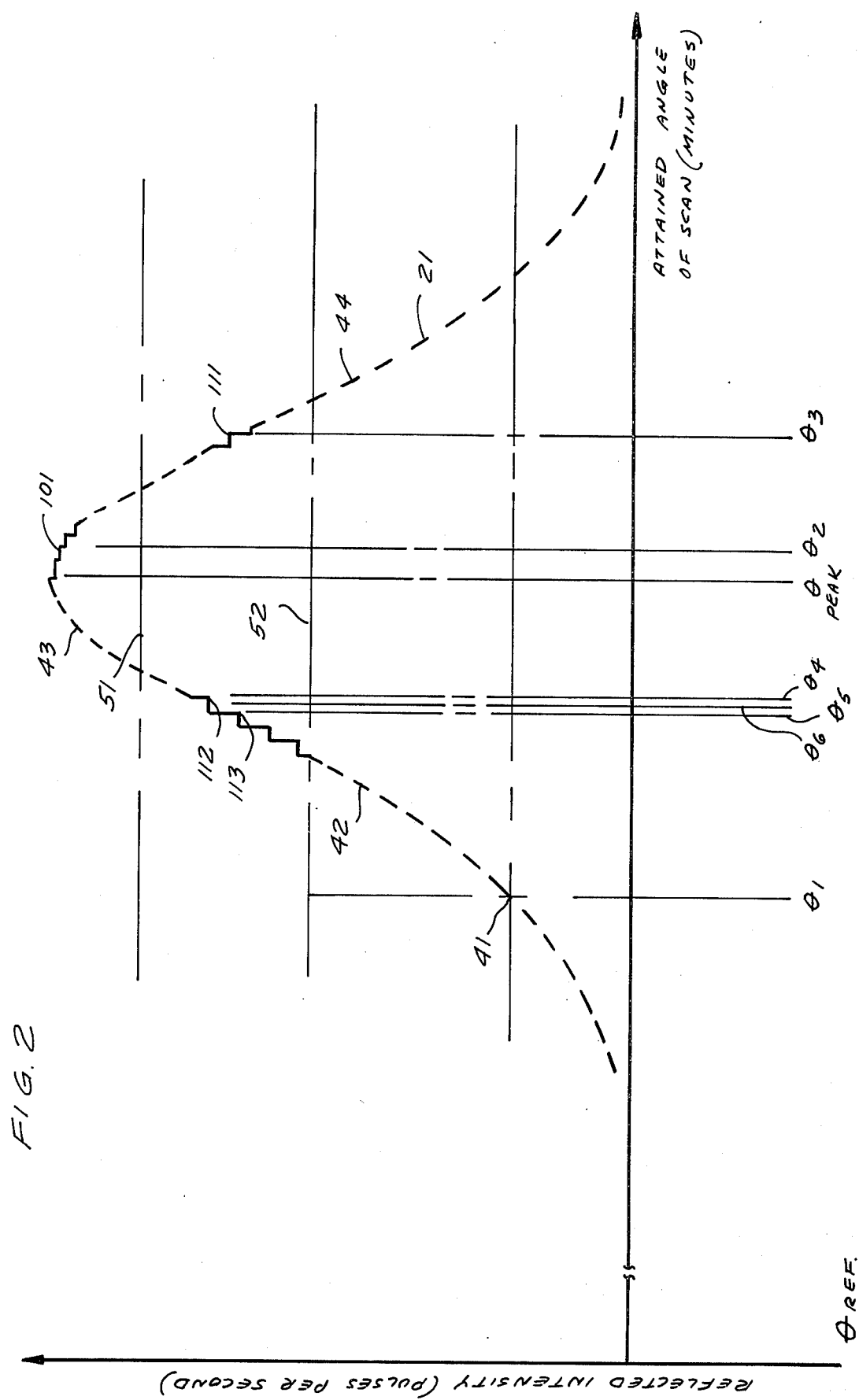
FIG. 2 is a curve representing the variation of reflected amplitude of the X-ray beam impinging on the crystal of FIG. 1 as the reference surface of the crystal is stepped over an angular range including the typically resonant-type response characteristic of the crystal.

The output of the detector 33 is applied through an amplifier 34 to the input of a peak approximating electronics unit 35, whose output is illustratively in the form of a binary indication of a suitably approximated peak angle of the response curve 21 (FIG. 2). The output of the unit 35 is applied to a suitable digital read-out device 36, and may also be applied to a suitable bin logic circuit (not shown) for discharging the tested crystal into a suitable compartment indicative of the determined peak angle of response.

The crystal on the mount 14 is scanned stepwise by a suitable stepping motor 40 over the angular range $\theta$ (FIG. 2), corresponding to an intensity level below a threshhold point 41, and proceeds successively over the threshhold 41, a leading edge 42, a peak region 43 and a trailing edge 44 of the crystal response characteristic 21. After each scan, the motor 40 can be suitably reversed and stepped back to the reference value for the next measurement.

The technique of the invention involves, in part, the assignment of a discrete range on both the leading and trailing edges of the response curve 21 over which the collected data representative of the intensity of reflection from the crystal is considered to be valid. Such valid data, in turn, is employed for the subsequent approximation of the desired angle of peak response.

Illustratively, the valid data region extends on both the leading and trailing edges of the characteristic 21 between an upper limit 51 denoting 87½% of a "peak" value approximated as indicated below, and a lower limit 52 indicative of a value 50% of such approximated peak value.

The data representative of reflection intensity is collected in the intervals between successive steps of the motor 40. Such intervals are made long enough so that the statistical error in the accumulation of pulses hitting the scintillation counter 33 is less than the difference in mean intensity between successive steps so that under normal circumstances an overlap of data over succeeding steps does not occur. Typically, when cut quartz crystals are inspected with the use of an X-ray tube having a copper target, a constant duration of about one-tenth sec. between successive steps (corresponding illustratively to 4.5 sec. of arc) over the valid data ranges of the characteristic 21 is sufficient to reduce the statistical error over successive steps to less than 0.5%.

Referring again to FIG. 3, the stepping motor 40 is driven by an adjustable reversible drive 61, which generates stepping pulses whose repetition interval is adjustable. Under the control of the drive 61, the stepping motor 40 executes three prescribed stepping movement: A first rapid movement at an illustrative 0.01 sec. repetition interval over the region of FIG. 2 extending from a reference angle $\theta_{ref}$ to an angle $\theta_1$ which yields an intensity indicate of a preset threshhold level 41 of the characteristic 21; a second relatively slow movement at an illustrative 0.1 sec. repetition interval over the remainder of the characteristic; and a return movement of the crystal mount 14 in the reverse direction to the reference position for the next measurement.

Control commands for the stepping motor drive 61 as well as for the peak approximating unit 35 are obtained from an operation sequencer 71, which may be adapted to execute the functions set forth in flow diagram form in Table 1 below. The successive operations dictated by the sequencer 71 are illustratively set forth in connection with FIGS. 4 and 5.

Figure 4:
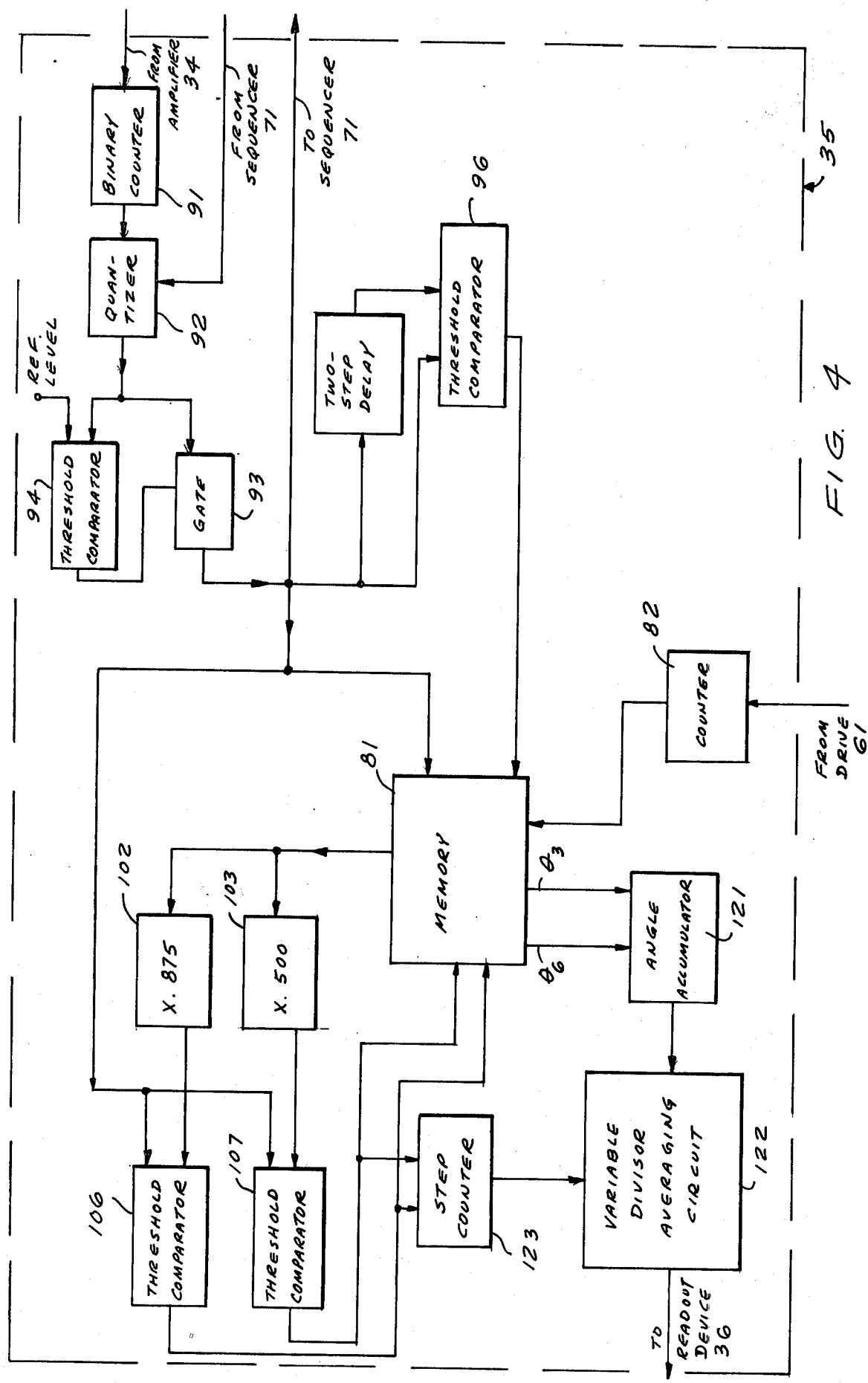
FIG. 4 is a block diagram of one embodiment of the peak approximating electronics of FIG. 3.

In the arrangement of FIG. 4, a conventional memory 81 is provided with an angle address block for storing digital indications indicative of the total attained angle $\theta$ of the crystal mount 14 as the crystal mounted thereon is scanned over its characteristic 21. For this purpose, each output stepping pulse from the driver 61 when such driver 61 operates in its slow-scan mode is also applied to a binary counter 82. The counter 82 provides a binary output whose successive values are coupled to the angle address block of the memory 81. Alternatively, the binary indications indicative of the successive attained angles of scan may be derived from a shaft encoder (not shown) coupled to the crystal holder 14.

The memory 81 also receives, in a separate intensity address portion thereof, binary indications of the intensity represented by the number of pulses integrated by the scintillation counter 33 at the conclusion of each step of the scan. For this purpose, the output of the scintillation counter 33 is applied to the input of a resettable binary counter 91 (FIG. 4) via the amplifier 34.

The counter 91 operates to count the pulses picked up by the scintillation counter 33 during the interval following each step of the crystal scan. The resulting output of the counter 91 is applied to a quantizer 92, which is pulsed at the step rate by the sequencer 71 to yield a succession of amplitude samples which individually indicate the total integrated pulses counted by the scintillation counter 33 over the associated interval.

The successive samples from the quantizer 92 are applied to the input of a normally disabled gate 93 and to one input of a threshhold comparator circuit 94. The other input of the circuit 94 is controlled by a reference level indicative of an intensity just below the threshhold value 41 of the characteristic 21. Thus, as soon as the crystal holder 14 has been stepped at its relatively high 0.01 sec. rate from its starting reference point $\theta_{ref}$ in FIG. 2 to the angle $\theta_1$, the then-occurring amplitude sample will exceed the present level applied to the threshhold circuit 94, and the circuit 94 will yield an output control pulse to enable the gate 93.

When the gate 93 is enabled, an output pulse therefrom is applied over line 95 to the sequencer 71, which then commands the motor driver 61 to decrease the stepping pulse repetition interval from 0.01 sec. to 0.1 sec. for the remainder of the scan. The succeeding amplitude samples from the quantizer 92 are applied through the now-enabled gate 93 to the intensity address block of the memory 81.

As the relatively slow step scan proceeds up the leading edge 42 of the response characteristic 21 beyond the threshhold level, the memory 81 accumulates the successive samples and the corresponding attained angle indications over a range encompassing the regions 42, 43 and 44 of the characteristic 21.

The output of the gate 93 is further applied directly to a first input of a second threshhold comparator circuit 96, and via a two-step delay circuit 97 to a second input of the circuit 96. Such circuit 96 is enabled whenever the amplitude applied to its second input falls below the amplitude applied to its first input; that is, the circuit 96 will be enabled whenever the amplitude samples successively applied through the gate 93 have decreased monotonically in amplitude over two successive steps. The amplitude sample at such instant is represented at 101 in FIG. 2, and corresponds to an attained angle $\theta_2$.

In further accordance with the invention, the amplitude of the stored sample occurring two steps prior to the occurrence of the triggering of the threshhold circuit 96 is taken as the peak value of the response characteristic 21. The output pulse generated by the threshhold circuit 96 is applied to the memory 81, and the memory responds to retrieve the stored sample corresponding to the "peak", i.e., the stored sample occurring two steps prior to the excitation of the threshhold circuit 96.

The retrieved "peak" sample is applied to a pair of multipliers 102 and 103, which respectively multiply the amplitude of the retrieved sample by the values .875 and .5, respectively. Such values are indicative of the upper and lower limits of the valid data range of FIG. 2. The output of the upper limit multiplying circuit 102 is applied to a reference input of a third threshhold comparator circuit 106, while the output of the lower limit multiplying circuit 103 is applied to a reference input of a fourth threshhold comparator circuit 107. Corresponding second inputs of the circuits 106 and 107 are excited by the output of the gate 93.

As the step scan proceeds down the trailing edge 44 of the characteristic 21 from the point 101, the successive samples from the gate 93 decrease in amplitude until the upper limit 51 of the valid data range is achieved. At this point, the threshhold comparator circuit 106 is triggered to apply a pulse to the memory 81.

The memory 81 responds to such pulse to initiate a "table scan" during each step that the successive samples from the gate 93 exhibit amplitudes within the valid data range on the trailing edge 44 of the characteristic 21. One such step, designated 111 in FIG. 2, has a corresponding attained angle $\theta_3$.

During each "table scan", the then-occurring step 111, applied to the memory from the gate 93, is compared with all the stored samples generated over the valid data range on the leading edge 42 of the response characteristic 21. Each such table scan is terminated upon the retrieval of a pair of successive stored samples (indicated 112 and 113), which are respectively greater and lesser in amplitude than the sample 111.

As indicated below in connection with FIG. 5, the respective attained angles $\theta_4$ and $\theta_5$ corresponding to each pair of successive samples 112 and 113 are also retrieved and suitably processed to derive an intermediate angle $\theta_6$, which corresponds to a reflected intensity value which approaches that of the sample 111. The table scans continue until the amplitude of the samples 111 have decreased in intensity to the point 52, at which time a scan stop pulse is applied to the memory from the threshhold circuit 107.

Each derived intermediate angle $\theta_6$ occurring on the leading edge 42 of the characteristic 21 is applied to one input of an angle accumulator 121. The other input of the angle accumulator receives an indication of the attained angle $\theta_3$ corresponding to the then-occurring sample 111 on the trailing edge 44 of the characteristic. The sums of the corresponding attained angles $\theta_6$ and $\theta_3$ are determined over all of the steps 111 in the valid data range on the trailing edge 44. In a typical case, 10 such sums are accumulated.

The accumulated output of the unit 121 is applied to a dividend input of a variable divisor averaging circuit 122. The divisor input of such circuit is coupled to the output of a step counter 123, which has a "start" input coupled to the threshhold circuit 106 and a "stop" input coupled to the threshhold circuit 107. Consequently, the output of the counter 123 represents the number of samples 111 in the valid data range.

The averaging circuit 122 effects a division of the accumulated sum from the unit 121 by twice the number of steps counted in the counter 123 to generate, in binary form, an indication of the angle of peak reflected intensity of the characteristic 21 of FIG. 2. As indicated above, such indication is applied to the read-out device 36 and to the notillustrated logic circuitry for determining the bin location in which the tested crystal is applied based on the so-determined peak angle and thereby on the corresponding Z—Z' angle.

Figure 5:
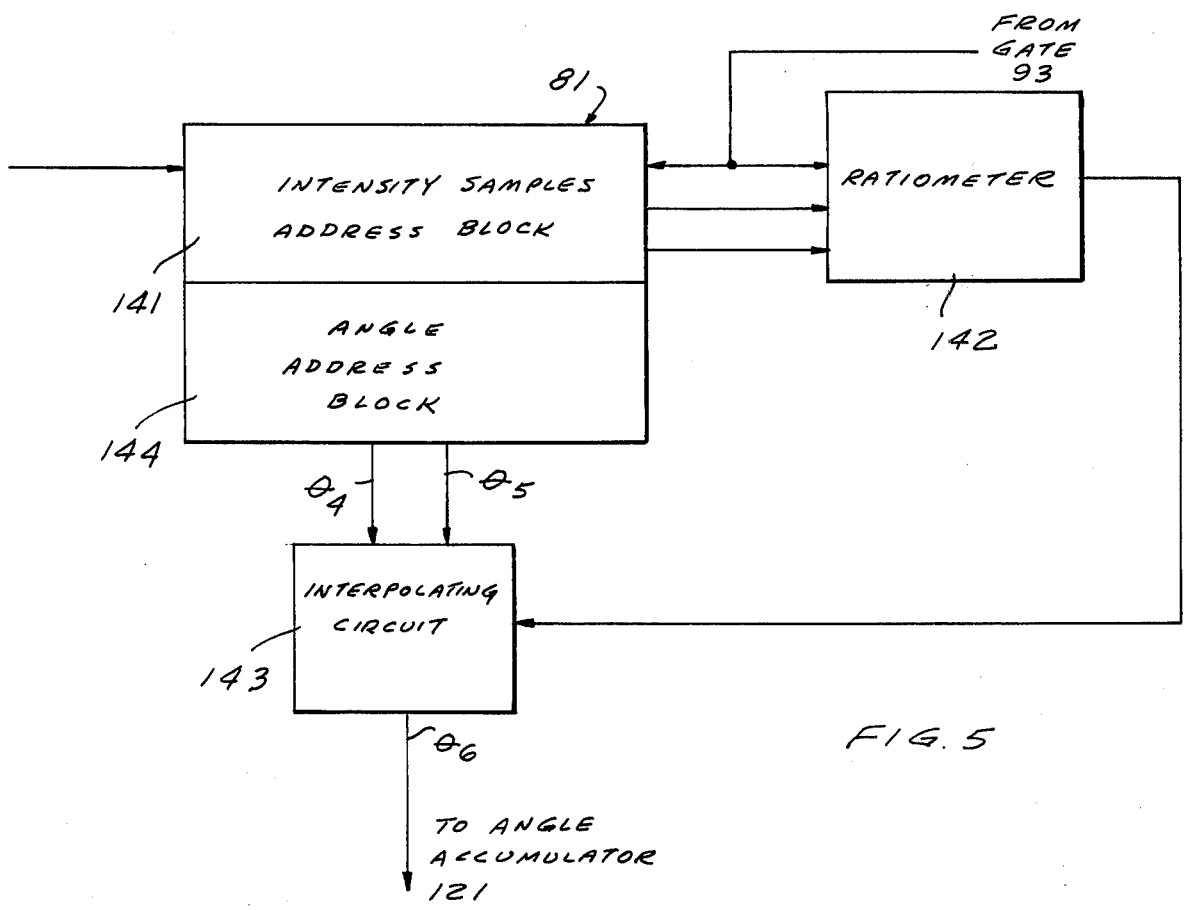
FIG. 5 is a block diagram of a portion of the circuitry of FIG. 4 suitable for interpolating between a pair of attained angles of scan.

One illustrative arrangement for deriving the intermediate angle $\theta_6$ for application to the angle accumulator 121 is shown in FIG. 5. During each table scan, the two values of the retrieved successive samples 112 and 113 are applied from the intensity sample address block (designated 141) of the memory 81 to first and second inputs of a ratiometer 142. The sample 111 is applied to a third input of the ratiometer 142. The ratiometer is adapted to assign a reference number of amplitude units between the values of the samples 112 and 113, and to calculate the difference in amplitude, in terms of such units, between the sample 111 and one of the samples 112 and 113. Finally, the ratiometer calculates the ratio of such amplitude difference to the total number of units between the values 112 and 113, and applies such ratio (advantageously in binary form) to a control input of an interpolating circuit 143.

The values to be interpolated in the unit 143 are the attained angles $\theta_4$ and $\theta_5$ corresponding to the then-retrieved samples 112 and 113, such angles being retrieved from the angle address block (designated 144) of the memory 81. The interpolating circuit 143 selects, between the angles $\theta_4$ and $\theta_5$, the intermediate angle $\theta_6$ whose position relative to the input angles corresponds to the ratio at the output of ratiometer 142. Such intermediate angle then corresponds closely to the amplitude of the sample 111, and is applied with the angle $\theta_3$ to the accumulator 121 for further processing as indicated above.

Without limiting the generality of the foregoing, Table 1 below illustrates a typical flow diagram of the above-mentioned sequence of operations controlled by the operation sequencer 71:

Table 1

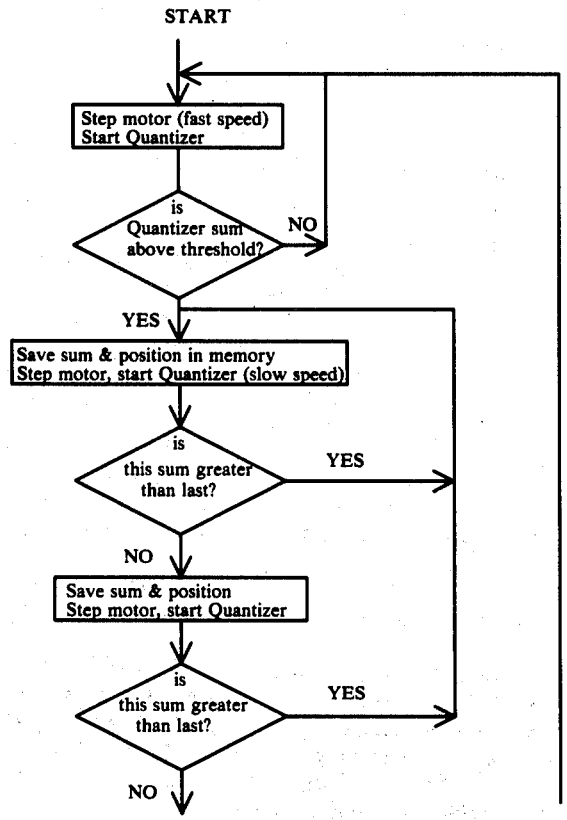

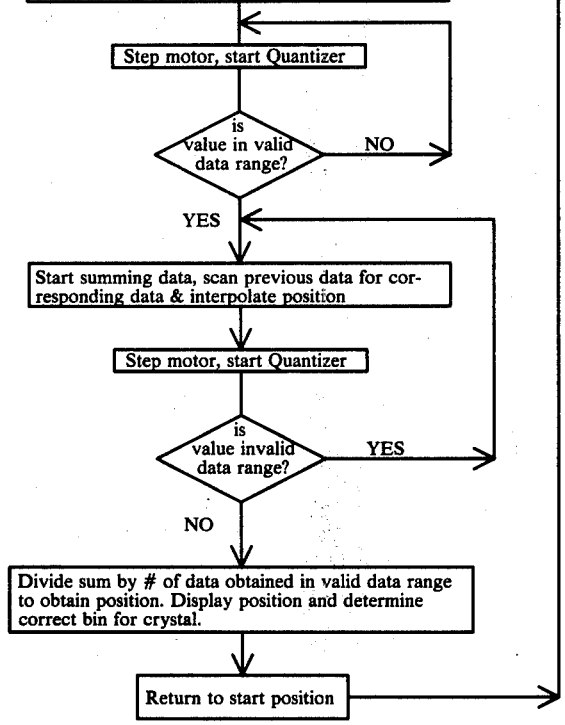

In the foregoing, an illustrative technique and arrangement of the invention have been described. Many variations and modifications will now occur to those skilled in the art. For example, the illustrative technique of the invention is not limited to the inspection of piezoelectric crystals, but can be applied to determine the peak response of many types of radiation-type sensitive resonant devices to a beam of radiation incident on a surface of the device as such surface is swept by the radiation beam. It is accordingly desired that the scope of the appended claims not be limited to the specific disclosure herein contained.

What is claimed is:

1. In a machine-instrumented method of determining the angle of peak amplitude response of a radiation-sensitive resonant device to a beam of radiation incident on a first surface of the device as the relative angle between the incident beam and the first surface is swept in a first direction, the improvement which comprises the steps of:
   scanning the first surface stepwise with the beam of radiation in the first direction;
   sampling the amplitude response of the device at the angle attained at the end of each step;
   storing successive ones of the measured amplitude samples;
   determining the attained angle of scan corresponding to each stored amplitude sample;
   determining the value of a first one of the attained angles occurring when the amplitude of the samples has decreased monotonically over a prescribed number of successive steps;
   retrieving a first one of the stored samples corresponding to a second one of the attained angles occurring the predetermined number of steps before the first attained angle;

calculating a predetermined amplitude value equal to a prescribed percentage of the retrieved first amplitude sample;

determining the value of a third one of the attained angles occurring when the samples have decreased in amplitude to the predetermined value following the first attained angle;

determining the value of a fourth one of the attained angles corresponding to the predetermined value and occurring before the second attained angle; and averaging the third and fourth attained angles to approximate the angle of peak response of the device.

2. In a machine-instrumented method of determining the angle of peak amplitude response of a radiation-sensitive resonant device to a beam of radiation incident on a first surface of the device as the relative angle between the incident beam and the first surface is scanned in a first direction over the response characteristic of the device, the improvement which comprises the steps of:

scanning the first surface stepwise with the beam of radiation in the first direction;

sampling the amplitude response of the device at the angle attained at the end of each step;

storing successive ones of the measured amplitude samples;

determining the attained angle of scan corresponding to each stored amplitude sample;

determining the value of a first one of the attained angles occurring when the amplitude of the samples has decreased monotonically over a prescribed number of successive steps;

retrieving a first one of the stored samples corresponding to a second one of the attained angles occurring the predetermined number of steps before the first attained angle; calculating a first predetermined amplitude value equal to a prescribed percentage of the first sample;

comparing, at the conclusion of successive steps starting with the step in which the amplitude of the samples has decreased to the first predetermined value following the first attained angle, the value of a then-occurring second one of the samples with a plurality of previously-stored third ones of the samples which individually correspond to third ones of the attained angles preceding the second attained angle, the third samples having amplitudes between the first predetermined value and a second predetermined value smaller than the first predetermined value;

determining, during each comparing step, the value of the stored third attained angle corresponding to the third sample which is closest to the then-occurring second sample;

adding each so-determined third attained angle to a fourth one of the attained angles corresponding to the thenoccurring second sample to form a first sum;

terminating the comparing steps when the second amplitude sample has decreased in amplitude to the second predetermined value, whereby the number of first sums obtained is equal to the number of steps occurring between the first predetermined value and the second predetermined value following the first attained angle;

adding the first sums to form a second sum; and dividing the second sum by twice the last-mentioned number of steps to approximate the angle of peak response of the device.

3. In a machine-instrumented method of determining the angle of peak reflection, from a prescribed internal atomic plane of a crystal, of a beam of radiation incident on the atomic plane through a reference surface of the crystal as the relative angle between the incident beam and the reference surface is scanned in a first direction over an angular range encompassing the response characteristic of the crystal to the beam, the improvement which comprises the steps of:

scanning the first surface of the crystal stepwise with the beam of radiation in the first direction;

sampling the amplitude of reflection of radiation from the crystal at the angle attained at the end of each step;

storing successive ones of the measured amplitude samples;

determining the attained angle of scan corresponding to each stored sample;

determining the value of a first one of the attained angles occurring when the amplitude of the samples has decreased monotonically over a prescribed number of successive steps;

retrieving a first one of the stored samples corresponding to a second one of the stored attained angles occurring the predetermined number of steps before the first attained angle;

calculating first and second predetermined amplitude values individually equal to first and second prescribed percentages of the amplitude of the retrieved first sample, the first percentage being greater than the second percentage;

comparing each of at least two second ones of the amplitude samples occurring after the first attained angle with a plurality of previously stored third ones of the samples which individually correspond to third ones of the attained angles preceding the second attained angle and which have amplitudes in the range between the first and second predetermined values, inclusive, the amplitudes of the second samples being in the range between the first and second predetermined values, inclusive;

determining, during each comparing step, the value of the stored third attained angle corresponding to the third sample whose amplitude is closest to the then-occurring second sample;

determining, during each comparing step, the value of a fourth one of the attained angles corresponding to the then-occurring second sample;

adding all the third and fourth attained angles resulting from the comparing steps; and dividing the resulting sum by twice the number of second samples to approximate the angle of peak reflection from the crystal.

4. A method as defined in claim 3, in which the prescribed number of successive steps is two.

5. A method as defined in claim 3, in which the first predetermined value is equal to 87½% of the amplitude of the first sample.

6. A method as defined in claim 5, in which the second predetermined value is equal to 50% of the amplitude of the first sample.

7. A method as defined in claim 3, in which the scanning step is accomplished by passing a fixed beam of the radiation through the reference surface as the reference surface is incrementally advanced in the first direction.

8. A method as defined in claim 3, in which the radiation comprises a beam of X-rays.

9. In a machine-instrumented method of determining the angle of peak reflection, from a prescribed internal atomic plane of a piezoelectric crystal, of a beam of radiation directed toward the atomic plane through the reference surface of the crystal as a relative angle between the incident beam and the first surface is swept in a first direction over an angular range encompassing the response characteristic of the crystal to said beam, the improvement which comprises the steps of:

scanning the reference surface stepwise with the beam of radiation in the first direction;

sampling the amplitude of the radiation reflected from the crystal at the angle attained at the end of each step;

storing the measured amplitude samples occurring after the amplitude response exceeds a first predetermined amplitude value;

determining the attained angle of scan corresponding to each stored amplitude sample;

determining the value of a first one of the attained angles occurring when the amplitude of the successive samples has decreased monotonically over a prescribed number of successive steps;

retrieving a first one of the stored samples corresponding to a second one of the attained angles occurring the predetermined number of steps before the first attained angle;

calculating a second predetermined amplitude value equal to a first prescribed percentage of the amplitude of the first sample;

calculating a third predetermined amplitude value equal to a second prescribed percentage of the amplitude of the first sample, the second percentage being lower than the first percentage;

comparing, at the conclusion of each successive step starting with the step in which the amplitude sample has decreased to the second predetermined value following the first attained angle, the amplitude of a then-occurring second one of the samples with a plurality of previously stored third ones of the samples which individually correspond to attained values preceding the second attained value and which have amplitudes in the range extending from the second predetermined value to the third predetermined value, inclusive;

retrieving, from each comparison, the successive pair of third samples having amplitudes immediately greater and less than the amplitude of the then-occurring second sample;

deriving, from the so-determined successive pair of third samples, the value of a third one of the attained angles occurring before the second attained angle and corresponding to the amplitude of the second sample;

adding each so-derived third attained angle to a fourth one of the attained angles corresponding to the then-occurring second sample to form a first sum;

terminating the comparison when the fourth sample had decreased in amplitude to the third predetermined value, whereby the number of first sums obtained is equal to the number of steps occurring between the second predetermined value and the third predetermined value following the occurrence of the first attained angle;

adding the first sums to form a second sum; and dividing the second sum by twice the last-mentioned number of steps to approximate the angle of peak reflection of the crystal.

10. A method as defined in claim 9, in which the deriving step comprises retrieving the values of the attained angles respectively corresponding to the determined successive third samples, determining the amplitude difference between the value of the then-occurring fourth sample and one of the corresponding retrieved third samples, and interpolating between the values of the determined attained angles corresponding to said determined successive third samples in accordance with the ratio of said determined amplitude difference to the actual amplitude difference between the successive third samples to obtain the third attained angle.

11. A method as defined in claim 9, in which the scanning step comprises stepping the beam of radiation at a relatively high angular rate from an initial angle spaced from the angular range of the device characteristic to an attained angle corresponding to the first predetermined amplitude value, and thereafter stepping the beam in the first direction at a relatively slow angular rate.

12. In an apparatus for determining the angle of peak reflection, from a prescribed internal atomic plane of a piezoelectric crystal, of a beam of radiation directed toward the atomic plane through a reference surface of the crystal as the relative angle between the incident beam and the reference surface is scanned over an angular range encompassing the response characteristic of the crystal, wherein the apparatus comprises a detector for measuring the amplitude of reflection from the crystal and means for indicating the instantaneous attained angle of the crystal during the scan, the improvement which comprises, in combination:

means for stepping the reference surface with respect to the beam of radiation to vary the output of the detector;

quantizing means operative at the stepping rate for sampling the output of the detector;

a memory;

means for coupling the successive samples from the quantizing means to the memory;

means coupled to the stepping means for coupling the output of the angle indicating means to the memory;

means including delay means responsive to the successive samples for generating a first indication when the amplitude of the successive samples has decreased monotonically over N successive steps;

first means associated with the memory and responsive to the first indication for retrieving a stored first one of the samples from the memory corresponding to a first one of the attained angles occurring N steps prior to the step in which the first indication is generated;

means coupled to the first retrieving means for individually multiplying the retrieved first sample by a first relatively high and a second relatively low prescribed fraction to obtain first and second predetermined values, respectively;

means associated with the storing means and rendered effective during each of a plurality of first steps when the amplitude of the successive samples lies between the first and second predetermined values following the generation of the first indication for scanning previously stored second ones of the amplitude samples occurring in the amplitude range extending between the first and second predetermined values, inclusive, and corresponding to attained angles preceding the first attained angle;

second means responsive to the first scanning means and operative during each of the first steps for retrieving a pair of successive values of the second samples that are respectively greater and less than the amplitude of a then-occurring third one of the samples;

third means rendered effective upon the retrieval of each of said pair of successive second samples for retrieving a pair of third successive attained angles corresponding to said pair of retrieved second samples;

means responsive to the second and third retrieving means for deriving a fourth one of the attained angles occurring between the successive pair of retrieved third angles;

means operative during the successive first steps for accumulating all the values of the successively derived fourth attained angles and the values of successive fifth ones of the attained angles corresponding to each third sample; and means for dividing the output of the accumulating means by twice the number of first steps to generate a quotient indicative of the angle of peak reflection of the crystal.

13. Apparatus as defined in claim 12, in which the means for coupling the samples to the memory includes normally disabled gating means rendered effective when the amplitude of the successive samples have attained a third predetermined value indicative of a threshold level of the crystal response characteristic.

14. Apparatus as defined in claim 12, in which the deriving means comprises, in combination, means for determining the relative amplitude difference between said then-occurring third sample and one of the correspondingly retrieved successive second samples, fourth means for retrieving the fifth pair of attained angles corresponding to the successive second samples, and means coupled to the output of the amplitude difference determining means and the fourth retrieving means for interpolating between said successive fifth angles in accordance with said relative amplitude difference to define the fourth one of said attained angles.

* * * * *